(12) United States Patent
Lacey et al.

(10) Patent No.: US 7,078,228 B2
(45) Date of Patent: Jul. 18, 2006

(54) CELL CULTIVATING FLASK

(75) Inventors: William J. Lacey, North Andover, MA (US); John A. Ryan, Clinton, MA (US); Laurence M. Vaughan, Westford, MA (US); Joseph C. Wall, Southborough, MA (US); Kathy M. Youngbear, Cambridge, MA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 10/750,474

(22) Filed: Dec. 31, 2003

(65) Prior Publication Data

US 2005/0148068 A1 Jul. 7, 2005

(51) Int. Cl.
*C12M 1/34* (2006.01)
(52) U.S. Cl. ............................. 435/288.1; 435/304.3
(58) Field of Classification Search ............. 435/288.1, 435/288.2, 304.1, 304.3, 305.1; D09/719, D09/741, 745, 504, 523, 526, 529, 573, 574, D09/575; D07/545
See application file for complete search history.

(56) References Cited

U.S. PATENT DOCUMENTS

| | | | | |
|---|---|---|---|---|
| 4,301,841 | A * | 11/1981 | Sandow | 141/98 |
| 4,839,292 | A | 6/1989 | Cremonese | 435/313 |
| 5,047,347 | A | 9/1991 | Cline | 435/296 |
| 5,801,054 | A | 9/1998 | Kiel et al. | 435/297.5 |
| 5,924,583 | A * | 7/1999 | Stevens et al. | 215/40 |
| 6,410,309 | B1 | 6/2002 | Barbera-Guillem et al. | 435/297.5 |
| 6,455,310 | B1 | 9/2002 | Barbera-Guillem | 435/383 |
| 6,479,252 | B1 | 11/2002 | Barbera-Guillem et al. | 435/41 |
| 2001/0055803 | A1 | 12/2001 | Wall et al. | 435/294.1 |
| 2003/0008388 | A1 | 1/2003 | Barbera-Guillem et al. | 435/297.5 |
| 2004/0029266 | A1 | 2/2004 | Barbera-Guillem | 435/297.5 |

FOREIGN PATENT DOCUMENTS

| | | |
|---|---|---|
| EP | 1 514 919 | 3/2005 |
| WO | WO 92/20779 | 11/1992 |
| WO | WO 98/27195 | 6/1998 |
| WO | WO 02/066595 | 8/2002 |

OTHER PUBLICATIONS

Maria E. Kempner et al., "A Review of Cell Culture Automation", JALA 2002.

* cited by examiner

*Primary Examiner*—David Redding
(74) *Attorney, Agent, or Firm*—Thomas R. Beall

(57) ABSTRACT

A stackable flask for the culturing of cells is disclosed. The cell culture chamber is defined by a top plate and a rigid bottom tray of substantially rectangular shape connected by side and end walls, the body of the flask has imparted therein a gas permeable membrane that will allow the free flow of gases between the cell culture chamber and the external environment. The flask body also includes a sealed septum that will allow access to the cell growth chamber by means of a needle or cannula. The size of the flask and location of an optional neck and cap section allows for flask manipulation by standard automated assay equipment, making the flask ideal for high throughput applications.

9 Claims, 6 Drawing Sheets

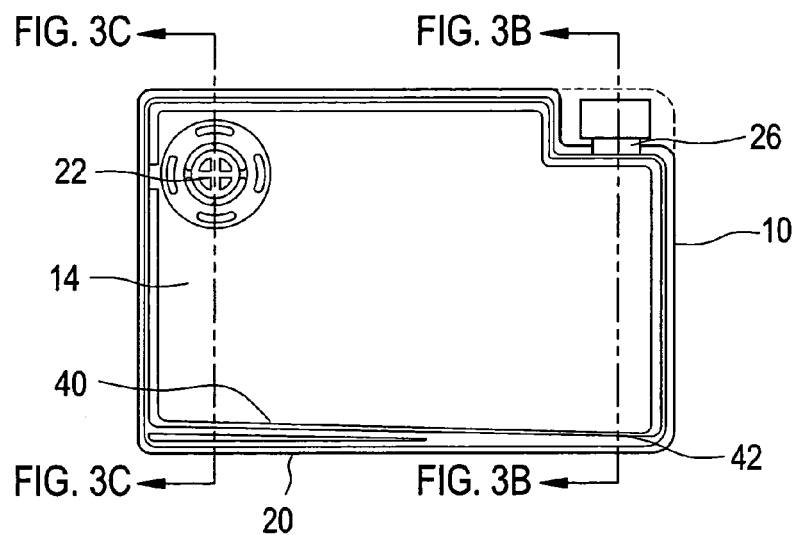
FIG. 3A
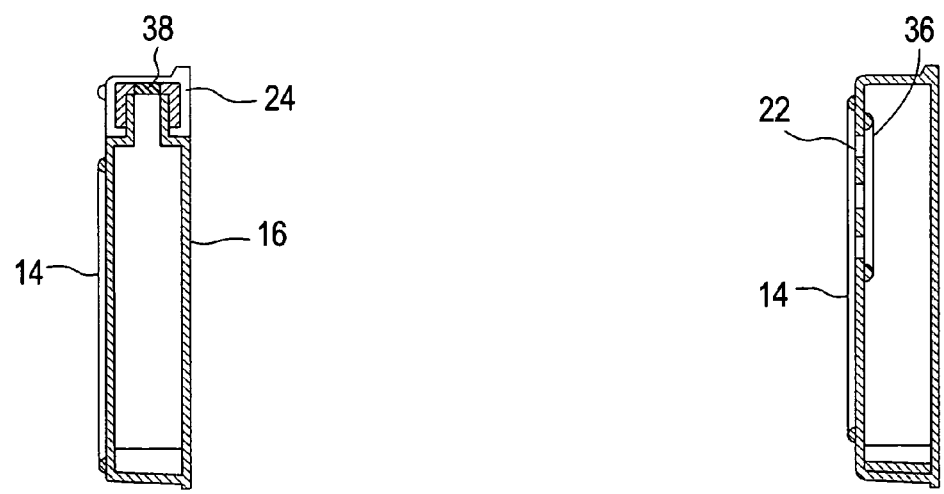
FIG. 3B
FIG. 3C

US 7,078,228 B2

CELL CULTIVATING FLASK

FIELD OF THE INVENTION

The present invention relates generally to the cellular biological field and, in particular, to a cell cultivating flask.

BACKGROUND OF THE INVENTION

In vitro culturing of cells provides material necessary for research in pharmacology, physiology, and toxicology. The environmental conditions created for cultured cells should resemble as closely as possible the conditions experienced by the cells in vivo. One example of a suitable medium for culturing cells is a common laboratory flask such as demonstrated in U.S. Pat. No. 4,770,854 to Lyman. The cells attach to and grow on the bottom wall of the flask, immersed in a suitable sustaining media. The flask is kept in an incubator to maintain it at the proper temperature and atmosphere.

Although most cells will tolerate a hydrogen ion concentration (pH) range of 6.8 to 7.8, the optimal pH for growth of mammalian cells is 7.2 to 7.4. For the optimal pH to be maintained during cell cultivation, the cell culture medium must contain a buffering system.

Frequently, pH is maintained by using a bicarbonate buffering system in the medium, in conjunction with an incubator atmosphere of approximately 5 to 7 percent carbon dioxide by volume. The carbon dioxide reacts with the water to form carbonic acid which in turn interacts with bicarbonate ions in the medium to form a buffering system which maintains the pH near physiological levels. Entry of carbon dioxide from the incubator into the cell culture flask is generally achieved by using a loosely fitting or vented cap or cover so that the small opening remains for the exchange of gas between flask and incubator. Further, flasks have been sold that are made from impact resistant polystyrene plastic which is permeable to water vapor, oxygen and carbon dioxide. However, relying only on the gas exchange through the polystyrene is generally ineffective since the permeability rate is so slow. Further still, flasks have been made having a cell growth surface that is itself an extremely thin (approximately 0.004 inches thick) flexible, gas permeable membrane. While this type of construction allows for gas exchange, the flexibility and thinness of the growth surface makes the growth of a uniform surface difficult and contributes to problems associated with the durability of the flask.

Desirably, many flasks are stacked together in the incubator and a number of cultures are simultaneously grown. Small variations in the growth medium, temperature, and cell variability have a pronounced effect on the progress of the cultures. Consequently, repeated microscopic visual inspections are needed to monitor the growth of the cells. As such, cell culture flasks are typically constructed of optically clear material that will allow such visual inspection.

With the advent of cell-based high throughput applications, fully automated cell culture systems have been the subject of serious development work (see e.g. A Review of Cell Culture Automation, M. E. Kempner, R. A. Felder, JALA Volume 7, No. 2, April/May 2002, pp. 56–62.) These automated systems employ traditional cell culture vessels (i.e. common flasks, roller bottles, and cell culture dishes). These systems invariably require articulated arms to uncap flasks and manipulate them much like the manual operator.

There is a need for a cell culture flask having a rigid structure that is capable of providing necessary gas exchange while being suitable for use in the performance of high throughput assay applications that commonly employ robotic manipulation.

SUMMARY OF THE INVENTION

According to an illustrative embodiment of the present invention, a flask for the efficient culturing of cells is disclosed. The illustrative flask includes a unitary body including a bottom tray defining a cell growth area and a top plate, connected by side walls and end walls. The body of the flask itself has at least one breathable membrane or film disposed therein. This membrane or film is permeable enough to prevent pressure differential between the flask interior and the external environment. For the addition and removal of media, the flask is equipped with a septum seal accessible opening or aperture either integrated within the body of the flask itself, or as a part of a cap. In addition, the flask of the present invention is shaped and configured to enable robotic access to the flask interior without requiring cumbersome robotic arm manipulation.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

FIG. 3(a) is a top view of an illustrative embodiment of the present invention.

FIG. 3(b) is a cross-sectional view along the cut line B—B of FIG. 3(a).

FIG. 3(c) is a cross sectional view along cut line C—C of FIG. 3(a).

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
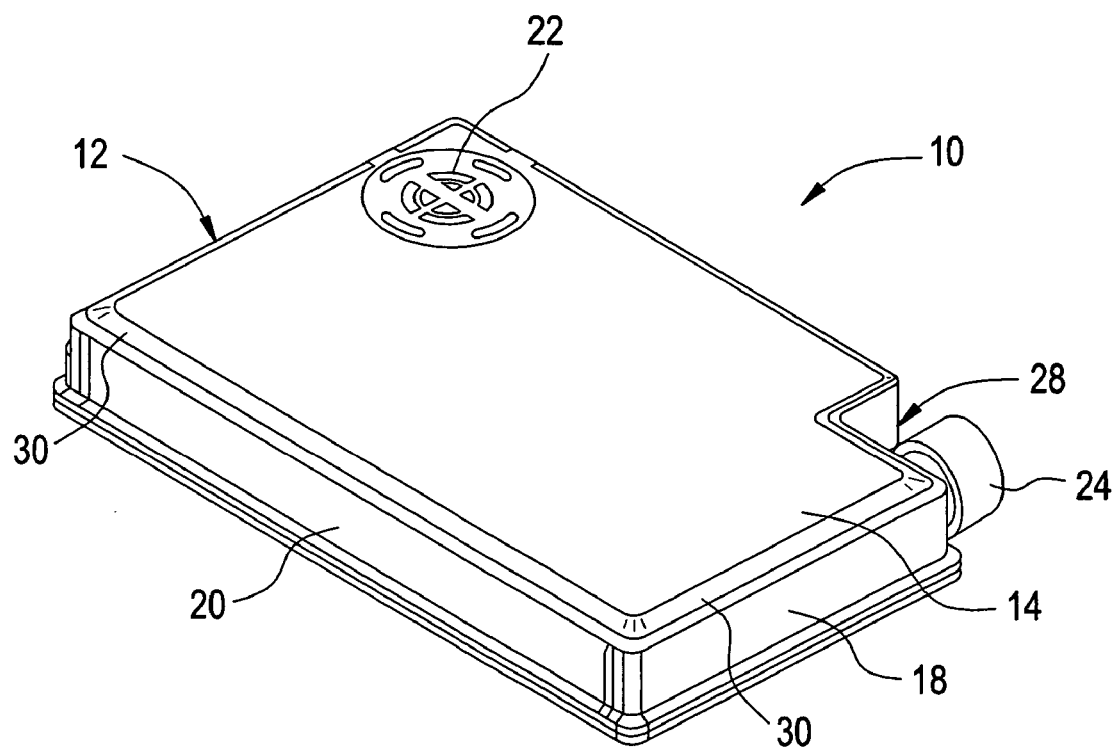
FIG. 1 is a perspective view of an illustrative embodiment of the flask of the present invention.
Figure 2:
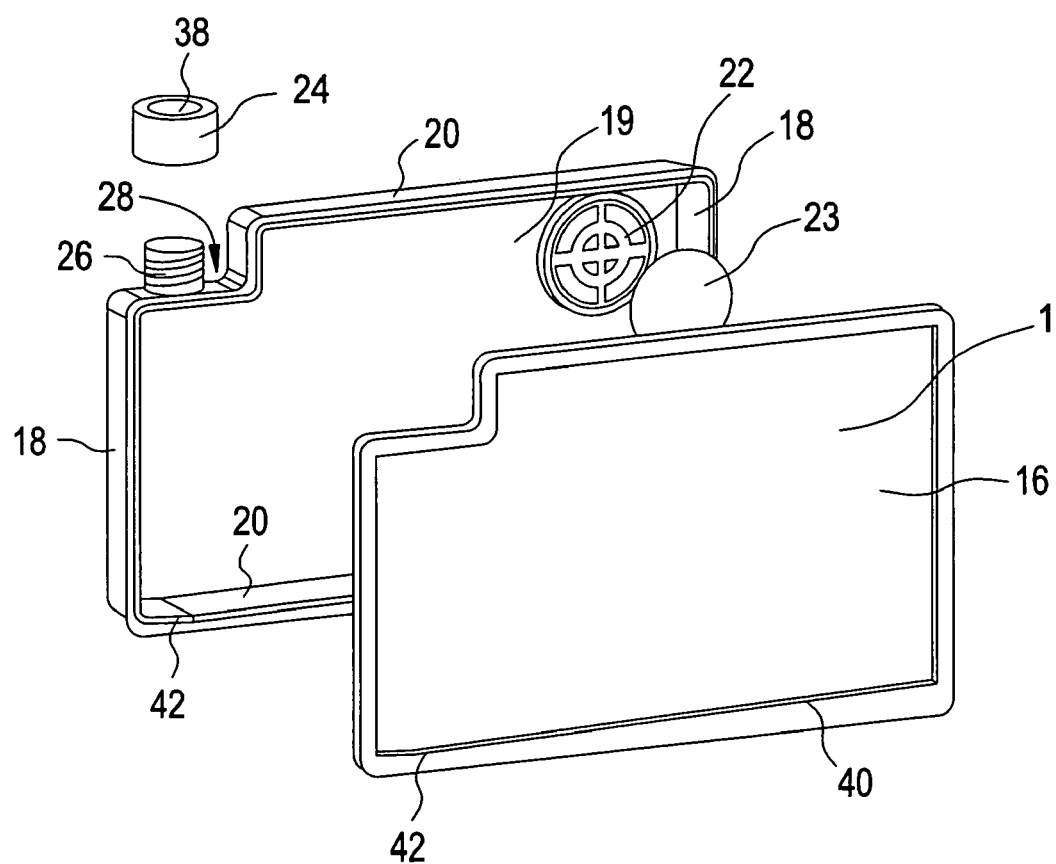
FIG. 2 is an exploded view of an illustrative embodiment of the present invention.
Figure 5:
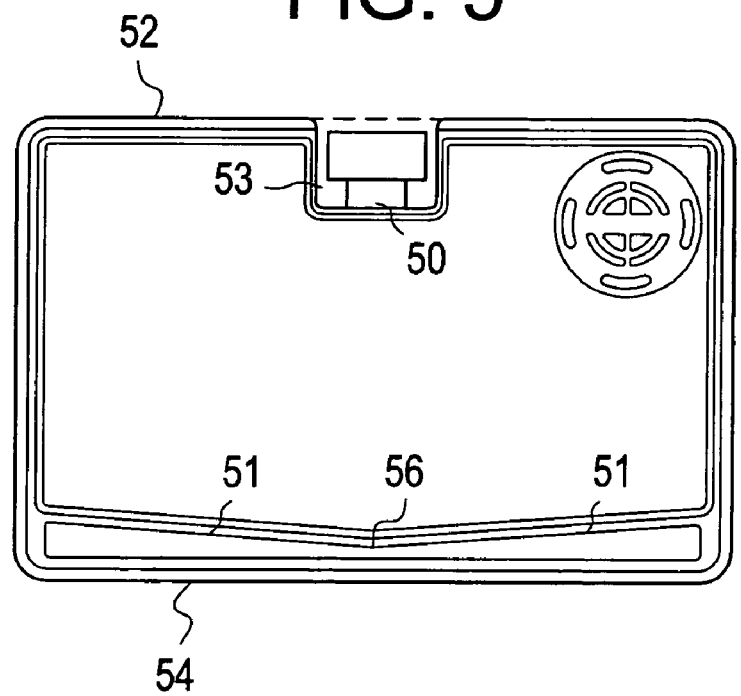
FIG. 5 is a top view of an alternate embodiment of the present invention.

Turning to FIGS. 1 and 2, a flask 10 of the present invention is shown. The flask body 12 comprises a top plate 14 and a bottom tray 16 defining a cell growth surface connected by sidewalls 18 and end walls 20. Disposed within the top plate of the flask is a vent 22. The vent protrudes slightly from the surface of the top plate 14 and is shaped to receive a disc 23 of gas permeable membrane material. It is made up of a series of openings through the flask body that will provide gaseous communication with the external environment. A necked opening 26 covered by a screw cap 26 is located within a notched corner 28 of the flask 10. As will be discussed in more detail below, the cap arrangement is preferably arranged such that the cap 24 does not protrude from the rectangular footprint of the flask. The rectangular footprint is the general length by width dimension occupied by the flask when the flask is placed on a surface such that the bottom tray contacts the surface and the top plate faces upwards as demonstrated in FIG. 1. For example, as shown in FIG. 3, the footprint is the area as determined by the periphery of the flask, with the periphery extended by the dashed line area around the notched corner 28. In FIG. 5, the flask footprint is defined by the flask periphery extended by the dashed line over the central notch 53.

Figure 7:
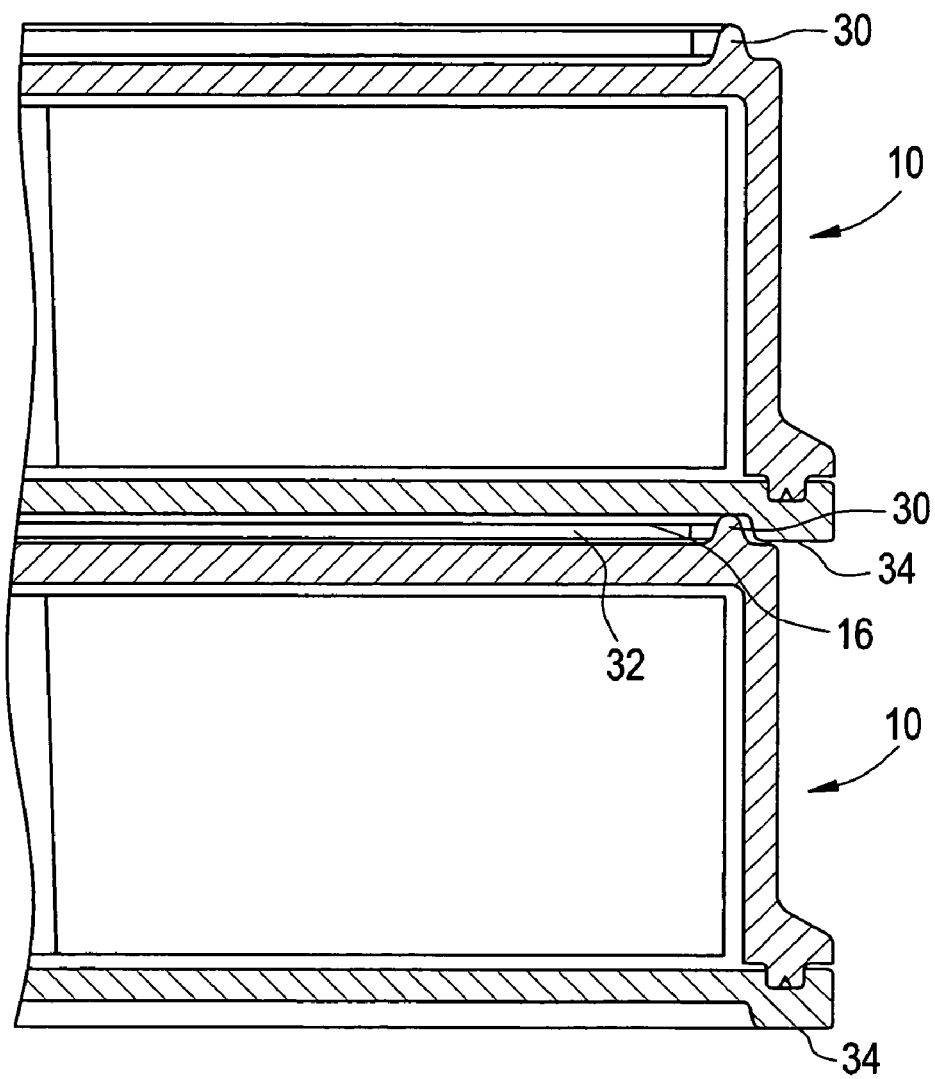
FIG. 7 is a partial cross sectional side view of two stacked flasks.

A raised rim 30 is located on the surface of the top plate serving as a standoff. Turning to FIG. 7, the standoff rim 30 is intended to contact the bottom tray 16 of an identical flask that is stacked on top the flask 10. Once stacked, the standoff rim allows an air gap 32 between stacked flasks, which is important to allow gas exchange through the vent. Other alternatives for standoffs include raised corners, posts, ledges, or any other feature that will allow spacing between successively stacked flasks. Further, the bottom plate preferably is molded with a rim 34 around the periphery that will engage with the standoff rim 30 from the immediately adjacent flask so as to ensure lateral stability of the stacked flasks.

The flask 10 may be made by any number of acceptable manufacturing methods well known to those of skill in the art. In a preferred method, the flask is assembled from a collection of separately injection molded parts. Although any polymer suitable for molding and commonly utilized in the manufacture of laboratory ware may be used, polystyrene is preferred. The separately molded parts may be formed from different polymers, but are preferably the same material. The bottom tray 16 is a substantially flat rigid piece having a thickness sufficient to provide stability and rigidity. For polystyrene, the thickness is preferably greater than 0.5 mm in thickness and more preferably greater than 1 mm. This thickness ensures that the flask bottom will be perfectly flat, which in use provides a durable surface that will readily attach a uniform cell layer. Although not required, for optical clarity, it is advantageous to maintain a thickness of no greater than 2 mm.

Advantageously and in order to enhance cell attachment and growth, the surface of the bottom tray is treated to make it hydrophilic. Treatment may be accomplished by any number of methods known in the art which include plasma discharge, corona discharge, gas plasma discharge, ion bombardment, ionizing radiation, and high intensity WV light. Although cell attachment is typically targeted for only one surface (the bottom tray), other parts of the flask may be treated so as to enable cell growth on all surfaces of the flask interior.

Like the bottom tray, the top plate is also preferably injection molded. The top plate preferably is molded such that the sidewalls 18, end walls 20, vent 22, and threaded neck 26 for receiving a cap 24 are molded together integrally. Also as shown in FIG. 3c, the vent is preferably molded with a locating ring 36 that extends from an inner surface of the top plate 14 and that will properly nest a membrane disc 23 on the interior portion of the vent structure.

A membrane disk 23 that has been punched from a sheet of membrane material is situated within the locating ring 36. The membrane disk 23 is properly sized so as to cover the entirety of the vent region 22 and to slightly overlap the portion of the top plate 14 surrounding the vent 22. The membrane disc 23 may be attached to the top plate 14 by any number of methods including but not limited to solvent bonding, ultrasonic welding, or heat welding. Heat welding around the circumference of the disc is preferred to establish a hermetic seal around the membrane region such that the membrane is flush with and fused to the face of the top plate such it becomes an integral portion of the interior surface of the flask. It is further preferred that the membrane be hydrophobic (non-wetting), or made from material that can be made hydrophobic by proper treatment methods. Examples of suitable materials include for example: polytetrafluoroethylene (PTFE), polyvinylidene fluoride (PVDF) or compatible fluoropolymer, or polypropylene. PTFE is the preferred material for the membrane. The membrane may be of any thickness, but ideally is between approximately 50 and 250 microns. Further, the membrane should preferably be capable of blocking the entrance or exit of bacteria and therefore will preferably have a porosity of between 0.2 microns and 0.45 microns, although larger pore sizes may be effective. The membrane and vent combination allow for the free and instantaneous exchange of gases between the interior of the flask and the external environment and are may take any size or shape.

Once the membrane is properly affixed to the vent area, the top plate and bottom tray may be joined. The parts are held together and are adhesive bonded along the seam, ultrasonically welded, or scan welded. Preferably, scan welding equipment is utilized in a partially or fully automated assembly system. The top plate and tray are properly aligned while a scan weld is made along the outer periphery of the joint.

Figure 6:
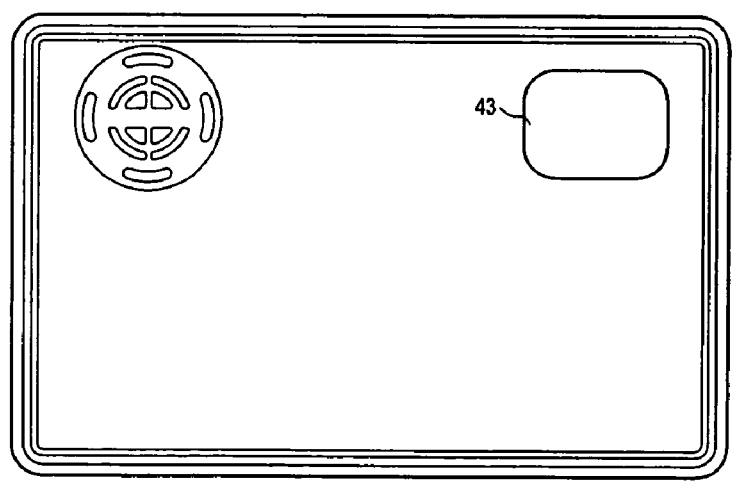
FIG. 6 is a top view of an alternate embodiment of the present invention.

Finally, a cap 24 is provided, preferably having a septum 38 that is integral with the cap top. This will allow a cannula, tip or needle to access the contents of the flask without the need for unscrewing. The septum 38 is leak proof, puncturable and capable of resealing once the needle, tip or cannula is removed from the flask, even after multiple punctures. It should be noted that a cap and neck arrangement is not necessary for the present invention. In another embodiment and as illustrated in FIG. 6, the septum 43 is integrally affixed to the body of the flask by any of the aforementioned methods for affixing a membrane disc to the flask wall. In such a case, access to the interior of the flask may be accomplished directly through the flask body through an aperture that is made impermeable to liquid by means of the septum 43. In this embodiment, the septum is preferably flush with the flask's outer surface and may be located in any surface of the flask body (sidewalls, end walls, top plate or bottom tray). There may also be multiple septum covering apertures thus allowing for multiple access points. This embodiment may be preferred when flask stacking is required, or when significant robotic manipulation is encountered since it eliminates the need for cap displacement. The septum itself may take any form well known to those of skill in the art including a slit arrangement useful for blunt needles and as generally described in WO 02/066595, the contents of which are incorporated herein by reference. Possible materials that may be employed in making the septum include natural and synthetic elastomeric materials including, but not limited to silicone rubber, fluoro-carbon rubber, butyl rubber, polychloroprene rubber, a silicone elastomer composite material, thermoplastic elastomer, medical grades of silicone rubber, polyisoprene, a synthetic isoprene, silicone and fluoropolymer laminate and combinations thereof. In a preferred embodiment, the elastomeric material is substantially nontoxic to cultured cells.

Due to the gas exchange through the flask body vent, pressure is equalized between the outside atmosphere and the flask interior even while removing or injecting liquid through the septum. As such the presence of the vent and appropriate membrane eliminates explosive spillage of contents due to pressure build-up.

Figure 4A:
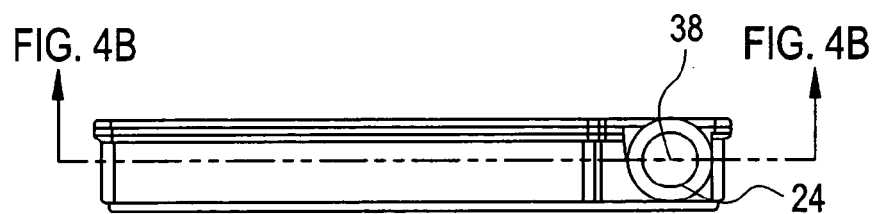
FIG. 4(a) is a top end side view of an illustrative embodiment of the present invention.
Figure 4B:
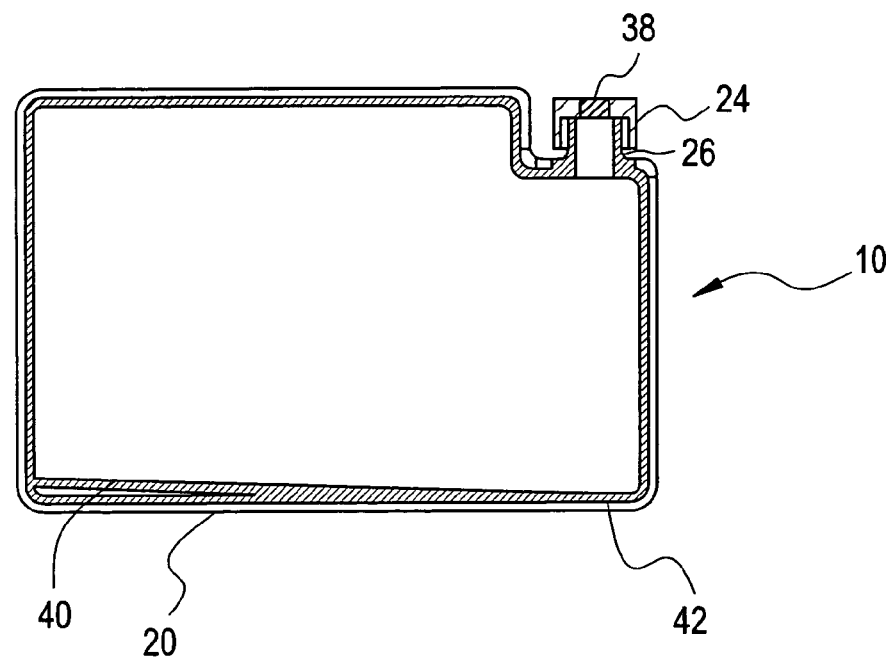
FIG. 4(b) is a cross-sectional view along cut line A—A of FIG. 4(a).

Another preferred element of the present invention is a sloping feature 40 along the end wall to enable complete drainage and removal of media when the flask is arranged in position in which the neck 26 faces upward. In such a position, media will pool at the bottom most portion 42 of the sloped end wall, which aligns vertically with the screw cap neck. For example, in FIGS. 3 and 4b, the left portion of the interior surface of the end wall 20 opposite the flask neck 26 is raised above the right side of the same end wall. The effect is that as the liquid is removed from the flask, the remaining media will pool in the lower most section 42. This allows for the complete removal of all liquid by means of a canulla extending vertically down from the neck and engaging the opposing end wall.

Although in the preferred embodiment, the neck is located in a corner of the flask, it should be noted that the neck region may be located anywhere along the flask's end wall or side wall. For example and as demonstrated in FIG. 5, the neck 50 may be located in the middle of the flask's end wall 52. In such an embodiment, two opposing slopes 51 making up the interior portion of an opposing end wall 54 converge in a bottom most point 56 that is located in vertical alignment with the necked portion 50.

In a preferred embodiment, the present invention has a footprint conforming with industry standard for microplates (5.030+/−0.010 inches by 3.365+/−0.010 inches). For this reason, the neck portion is preferably recessed within the overall rectangular footprint. The advantage of providing a flask with such a footprint is that automated equipment designed specifically for the manipulation of microplates may be utilized with this flask with very little customized modification. Similarly the height, or the distance between the outer most portion of the bottom tray and the outer portion of the top plate, is approximately 0.685+/−0.010 inches. As demonstrated in FIG. 3b and FIG. 4a, the neck 26 and cap 24 do not extend beyond the footprint of the flask. At any rate, the present invention is not intended to be limited in any way by the aforementioned preferred dimensions and in fact may be constructed to any dimension.

In use, the flask of the current invention is employed according to accepted cell growth methods. Cells are introduced to the flask though the threaded neck or through the septum. Along with the cells, media is introduced such that the cells are immersed in the media. The flask is arranged such that the cell containing media covers the cell growth surface of the bottom tray. It is important not to completely fill the flask so as not to cover the membrane/vent combination. This will ensure the free and rapid exchange of gases between flask interior and the external environment. The flask is then placed within an incubator and may be stacked together with similar flasks such that a number of cell cultures are simultaneously grown. The flask is situated such that the bottom tray assumes a horizontal position that will allow it to be completely covered by media. Cell growth is monitored from time to time by microscopic inspection through the bottom tray. During the cell growth process, it may become necessary to extract the exhausted media and insert fresh media. As previously described, media replacement may be achieved through insertion of a cannula, for example, through the septum. Alternatively, the media may be replaced by removing the cap, in embodiments that offer this option. Once the cells are ready for harvesting, a chemical additive such as trypsin is added to the flask through the septum. The trypsin has the effect of releasing the cells from the flask walls. The cells are then harvested from the flask.

The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

We claim:

1. A flask for the growth of cells comprising:
    a flask body serving as a cell culture chamber defined by a bottom tray having a rigid surface and a top plate, the bottom tray and top plate connected by side walls and end walls,
    the flask body having a substantially rectangular footprint,
    at least one gas permeable insert located within the flask body defining a gas permeable opening through which gases from within the cell culture chamber communicate with gases outside the cell culture chamber,
    a neck connected to and extending from the flask body, the neck having an opening providing access to the cell culture chamber,
    a cap for covering said neck opening,
    a cut-out region from said substantially rectangular footprint,
    whereby the neck and cap extend from the flask within the cut-out region such that the neck and cap remain within the substantially rectangular footprint.

2. The flask of claim 1 further comprising at least one gas permeable insert located within the flask body defining a gas permeable opening through which gases from within the cell culture chamber communicate with gasses outside the cell culture chamber.

3. The flask of claim 1 wherein the insert is a hydrophobic membrane.

4. The flask of claim 1 further comprising a septum located within a top surface of the cap.

5. The flask according to claim 1 wherein the rectangular footprint has dimensions that are substantially identical to the industry standard footprint dimension for microplates.

6. The flask according to claim 1 further comprising stand-offs either rising from an exterior surface of the top plate or descending from an exterior surface of the bottom tray.

7. The flask according to claim 1 wherein the flask has a height as measured by the distance between an outermost plane of the bottom tray and an outermost plane of the top plate, and wherein the cap has a diameter that does not exceed the height of the flask.

8. The flask according to claim 1 wherein said neck is located along one wall and an interior portion of an opposing wall is sloped in such a way that when the flask is situated with the neck facing upwards, the lowest most point of the opposing sidewall is located in vertical alignment with the neck.

9. The flask according to claim 1 further comprising a vent integrally molded within the top surface, whereby the vent is capable of supporting the insert and whereby the insert covers the vent such that liquid may not escape the cell culture chamber through the vent.

* * * * *